US006978286B2

(12) United States Patent
Francis et al.

(10) Patent No.: US 6,978,286 B2
(45) Date of Patent: Dec. 20, 2005

(54) HANDHELD MEDICATION DOSAGE CALCULATOR

(75) Inventors: Katharine R. Francis, Dunlap, IL (US); Diane M. Mathis, Springfield, IL (US)

(73) Assignee: Francis Mathis, Inc., Dunlap, IL (US)

( * ) Notice: Subject to any disclaimer, the term of this patent is extended or adjusted under 35 U.S.C. 154(b) by 184 days.

(21) Appl. No.: 10/478,576

(22) PCT Filed: Aug. 27, 2002

(86) PCT No.: PCT/US02/27269

§ 371 (c)(1),
(2), (4) Date: Nov. 24, 2003

(87) PCT Pub. No.: WO03/019332

PCT Pub. Date: Mar. 6, 2003

(65) Prior Publication Data
US 2004/0143346 A1    Jul. 22, 2004

Related U.S. Application Data

(60) Provisional application No. 60/315,145, filed on Aug. 27, 2001, provisional application No. 60/335,684, filed on Oct. 31, 2001.

(51) Int. Cl.[7] ............................................... G06F 3/00
(52) U.S. Cl. ..................... 708/132; 708/200; 705/3; 700/80; 700/83; 700/233; 700/240; 340/573.1; 600/300
(58) Field of Search ................... 700/80, 83, 231–233; 700/240–244; 705/2, 3; 708/130–132, 200; 340/573.1; 600/300

(56) References Cited
U.S. PATENT DOCUMENTS

| | | | |
|---|---|---|---|
| 3,878,496 A | 4/1975 | Erickson | |
| 4,428,050 A | 1/1984 | Pellegrino et al. | |
| 4,709,331 A | 11/1987 | Barkett et al. | |
| 4,807,170 A | 2/1989 | Kulli et al. | |
| 5,104,374 A * | 4/1992 | Bishko et al. | ................ 604/65 |
| 5,609,575 A | 3/1997 | Larson et al. | |
| 5,960,403 A * | 9/1999 | Brown | ......................... 705/2 |
| 6,000,828 A * | 12/1999 | Leet | ............................. 705/2 |
| 6,167,412 A | 12/2000 | Simons | |
| 6,589,169 B1 * | 7/2003 | Surwit et al. | ............... 600/300 |
| 6,594,634 B1 * | 7/2003 | Hampton et al. | .............. 705/3 |
| 2002/0010429 A1 * | 1/2002 | Grogan, Jr. | |
| 2002/0107501 A1 | 8/2002 | Smith et al. | |
| 2002/0116222 A1 * | 8/2002 | Wurster | |
| 2002/0130779 A1 * | 9/2002 | Ford | |
| 2003/0019115 A1 * | 1/2003 | Tannenbaum | |
| 2004/0064342 A1 * | 4/2004 | Browne | |
| 2004/0230457 A1 * | 11/2004 | Rosenbloom et al. | |

* cited by examiner

*Primary Examiner*—Wilbert L. Starks, Jr.
*Assistant Examiner*—Crystal J Barnes
(74) *Attorney, Agent, or Firm*—Husch & Eppenberger, LLC; Robert C. Haldiman

(57) ABSTRACT

A handheld medication dosage calculator (100) and method for comparing an inputted, ordered medication dosage with a known medication dosage range in a database including an input device for inputting a desired drug name, indicating whether the drug is for a child or an adult, an amount of the drugs that are ordered, the body weight or body surface of the patient, an amount of drug available in standard packaging, and the available volume associated with the available drug and a computing mechanism for determining the dosage of the drug to be delivered. The handheld medication dosage calculator (100) provides warnings when the inputted amount of drug exceeds the dose range limits or is incorrect. The handheld medication dose range calculator (100) converts an inputted drug unit of measure into a desired unit of measure. The handheld medication dosage calculator (100) lists generic drug names, trademarked product names, drug classifications and cautionary drug warning information.

24 Claims, 9 Drawing Sheets

HANDHELD MEDICATION DOSAGE CALCULATOR

CROSS REFERENCE TO RELATED APPLICATIONS

This application claims priority of prior Provisional Application Nos. 60/315,145 and 60/335,684, filed 27 Aug. 2001 and 31 Oct. 2001, respectively.

TECHNICAL FIELD OF THE INVENTION

The present invention relates to medical computers and handheld medical calculators and, more specifically, an apparatus and method for calculating medication dosages and for comparing an ordered, inputted dosage with a database having a recommended known medication dosage range and for providing cautions and warnings for the administration of a particular medication.

DESCRIPTION OF THE RELATED TART

The incidence of medication errors is a widely known problem in the medical industry. Most medications that are administered in the institutional setting are carefully checked for: 1) a correct physician order according to known drug dosage ranges; 2) a correct drug dosage calculation of the amount ordered per the amount available in standard packaging; and 3) cautions and warnings pertaining to the administration for that drug. These checks commonly occur in institutional pharmacies and are the standard of care in the industry. However, there are times when this system of checking medications in the pharmacy before dispensing the medication to the nursing unit is not feasible. For instance, in the neonatal intensive care unit, the nurse must calculate the dosages for many drugs that are to be administered at the time of administration. In the surgical and cardiac intensive care setting, drug dosages are changed frequently and are often calculated by,the nurse or physician at the patient's bedside. In the case of any medical emergency, such as cardio-respiratory arrest or shock, emergency medications are obtained from the emergency stock on hand in the patient care unit and calculated at the time of administration by the caregiver. In all cases, nurses and other health care givers are required to perform these calculations based on formulas committed to memory. Although the calculations are usually performed on a standard handheld mathematical calculator, there remains room for a high margin of error. First, there is a proper sequence of equations that are essential to obtaining the correct answer. Second, the equations often require conversion of various dimensional units (e.g., micrograms to milligrams, pounds to kilograms and so forth). These conversions must be calculated and then recorded or recalled for use in a later sequence of the equation. Third, knowledge of correct dosage ranges, cautions and warnings must be known to the medical professional for that person to safely administer the medication. The likelihood of all three of these factors being reliably drawn from the memory of the medical professional is understandably reduced under stressful situations such as a medical emergency or a sudden change in patient status.

A device that attempts to address a limited portion of the stated problems includes that disclosed in U.S. Pat. No. 6,167,412, which issued to Simons on Dec. 26, 2000. This handheld device prompts the user to complete drug dosage and infusion calculations. This device includes a memory containing drug dosage information that is accessed by the user. This device does not link the input calculations with a drug database and does not provide a warning or a caution notification when an incorrect input has been entered. Although the device does complete the required calculation for the user, it does not provide the user with an on-screen, intuitive format for entering input data. The user of the device must rely on memory in order to recall the proper sequence of keypad compression to complete the various calculations. As a result, there is very little improvement over a standard calculator. The user's reliance on his or her memory is not significantly reduced and there is no system to alert the user of potential errors in the prescribed dose or alert the user regarding potentially harmful drug, cautions and warnings if the user neglects to access the drug information database.

The present invention is directed to overcoming one or more of the problems set forth above.

BRIEF SUMMARY OF THE INVENTION

In one aspect of this present invention, an improved handheld medication dosage calculator is disclosed. This handheld medication dosage calculator includes an input device for inputting a desired drug name, inputting an indication as to whether the drug is for a child or an adult, inputting an amount of the drug that is ordered, inputting the body weight or body surface area of the patient, inputting an amount of drug that is available in standard packaging, and inputting the available volume associated with the amount of the available drug and a computing mechanism for determining the appropriate dosage of the drug that is to be delivered to the patient.

In another aspect of this present invention, a method for calculating medication dosages is disclosed. This method includes inputting a desired drug name, inputting an indication as to whether the drug is for a child or an adult, inputting an amount of the drug that is ordered, inputting the body weight or body surface area of the patient, inputting an amount of drug that is available in standard packaging and inputting the available volume associated with the amount of the available drug with an input device and determining the appropriate dosage of the drug that is to be delivered to the patient with a computing mechanism.

Yet another aspect of this present invention is to provide cautionary warnings associated with a selected drug.

Still another aspect of this present invention is to provide the generic name for a selected drug.

Another aspect of this present invention is to provide the trademarked product name for a selected drug.

Yet another aspect of this present invention is to provide the classification for a selected drug.

In another aspect of this present invention warnings are provided when the inputted amount of the drug exceeds the dosage range limits or is incorrect.

Still another aspect of this present invention is to convert inputted drug measurement units into desired units of measurement.

Yet another aspect of this present invention is to provide an intuitive input for the information that greatly reduces the need for the user to rely on his or her memory in performing the sequence of keypad operations on the handheld medication dosage calculator.

These are merely some of the innumerable illustrative aspects of this present invention and should not be deemed an all-inclusive listing.

BRIEF DESCRIPTION OF THE DRAWINGS

For a better understanding of the present invention, reference may be made to the accompanying drawings in which.

DETAILED DESCRIPTION OF THE INVENTION

In the following detailed description numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. For example, the invention is not limited in scope to the particular type of industry application depicted in the figures, a particular type of software language, or to particular conventions regarding software designations. The calculator or computing mechanism referred to in this patent application can be performed with a single integrated circuit or can be the result of the functioning of an entire series of complex microprocessors. The preferred method of communication to download the latest drug-related information associated with this invention is through a global computer network, e.g., Internet; however, there are numerous mechanisms for electronic communication that might suffice for this present invention.

Figure 1A:
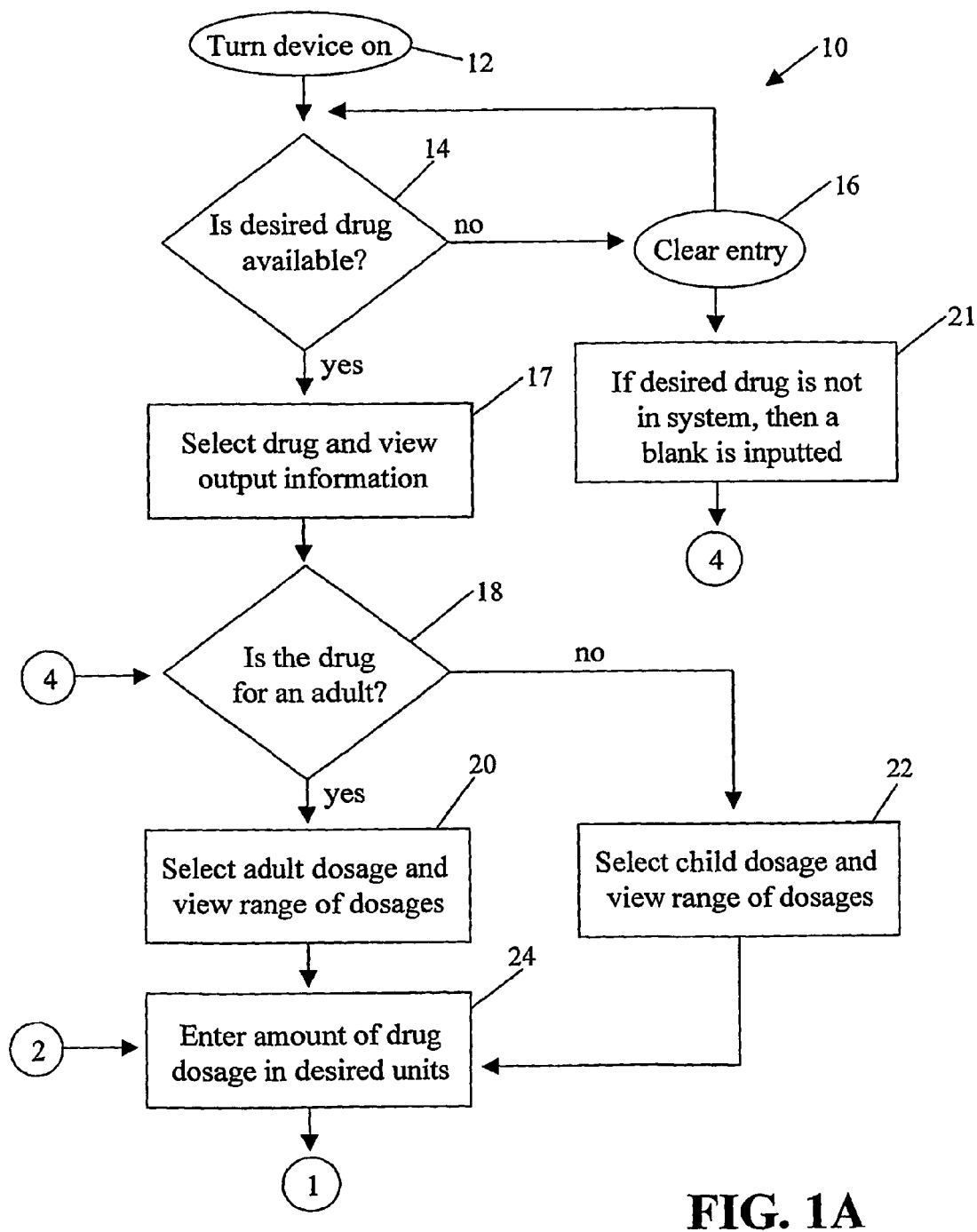
FIGS. 1A, 1B and 1C illustrate a schematic process diagram of tie handheld medication dosage calculator associated with the present invention.
Figure 1B:
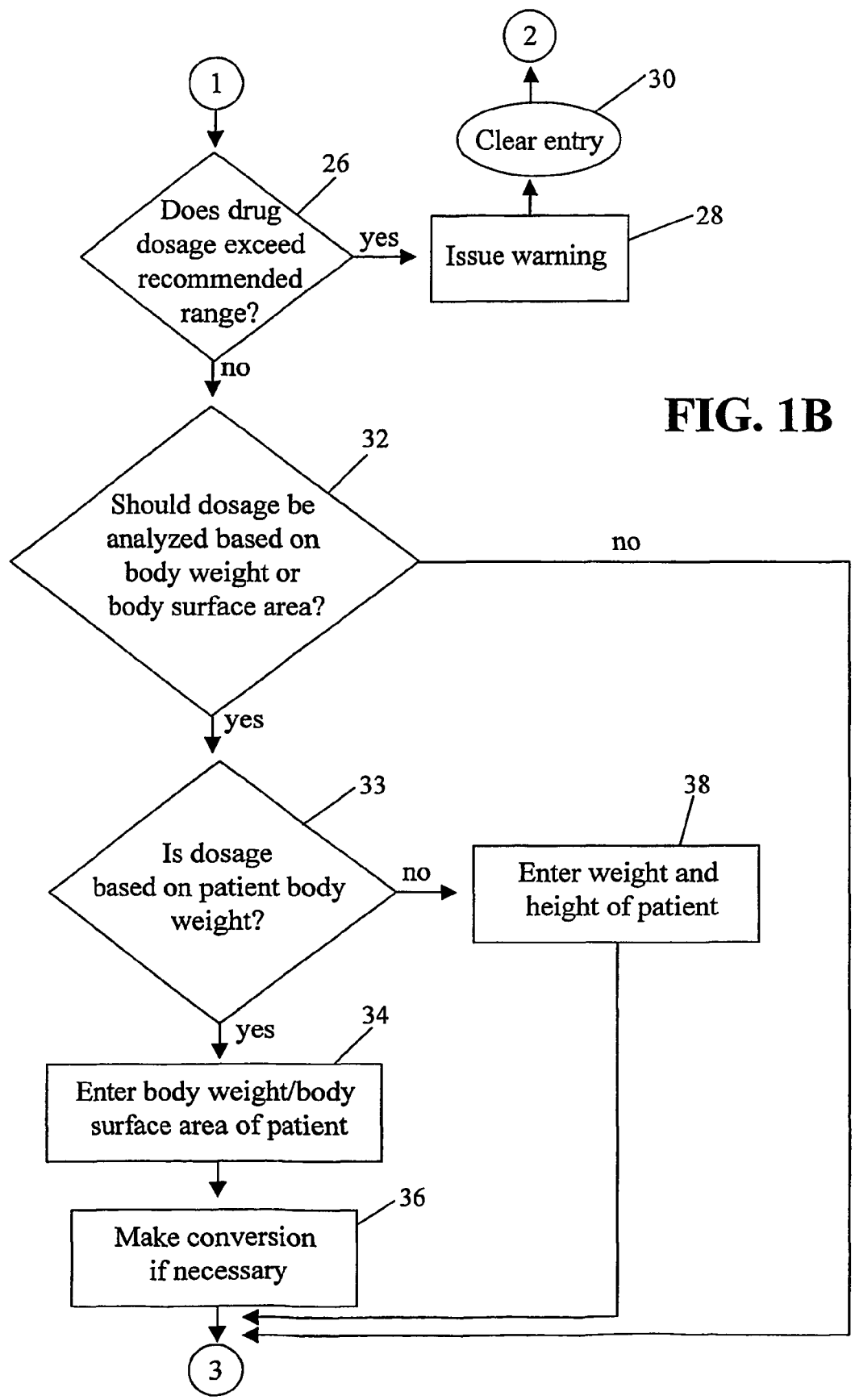
Figure 1C:
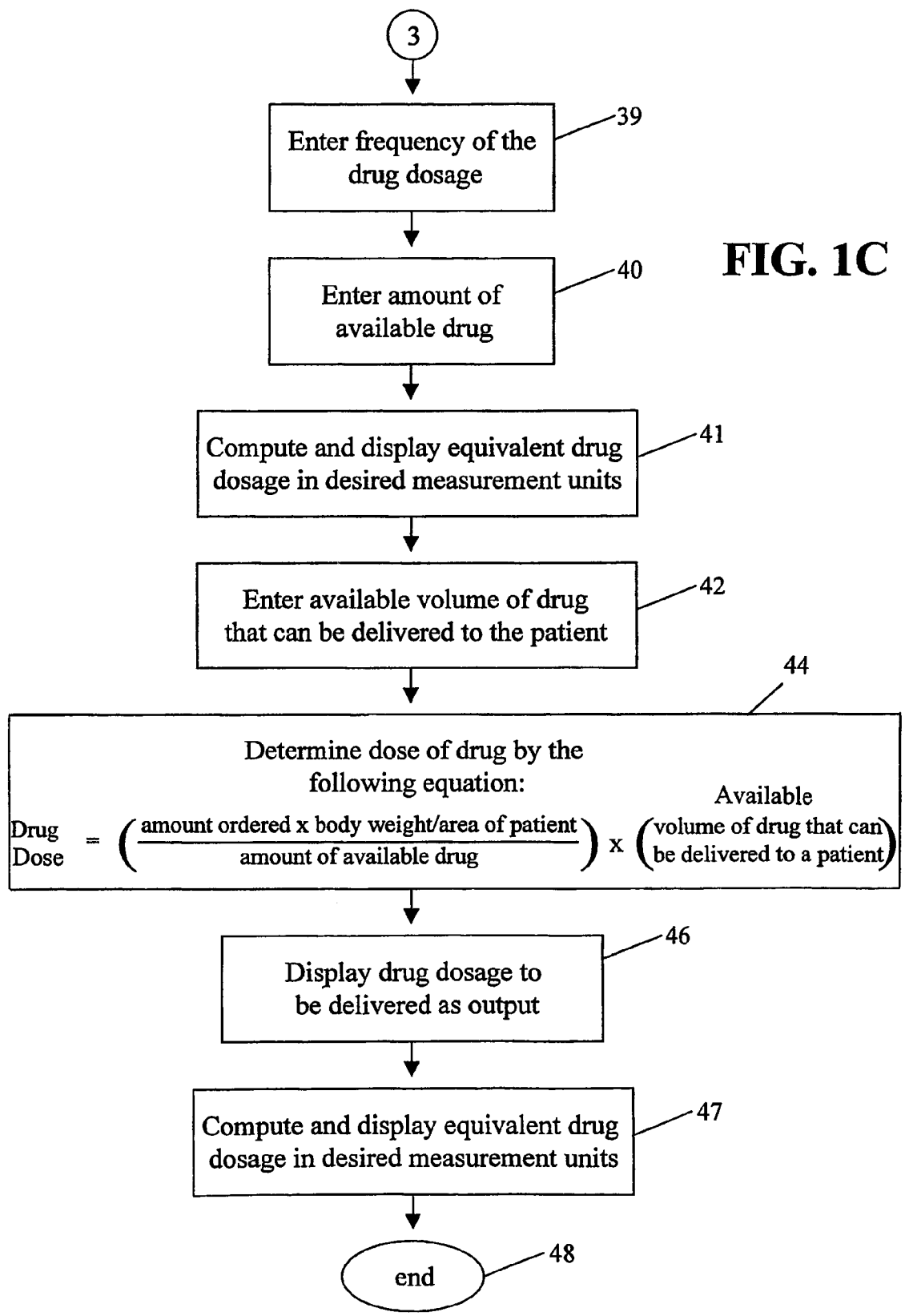

Referring now to the drawings, and initially to FIGS. 1A, 1B and 1C, which illustrate a flowchart of the handheld medication dosage calculator of the present invention and is denoted generally by reference numeral 10. A programmer skilled in the art could utilize this flowchart to program any of a wide variety of electronic controllers/computers in a wide variety of programming languages. In the description of the flowchart in FIGS. 1A, 1B and 1C, the functional explanation marked with numerals in angle brackets, <nnn>, will refer to the flowchart blocks bearing that number.

Figure 4:
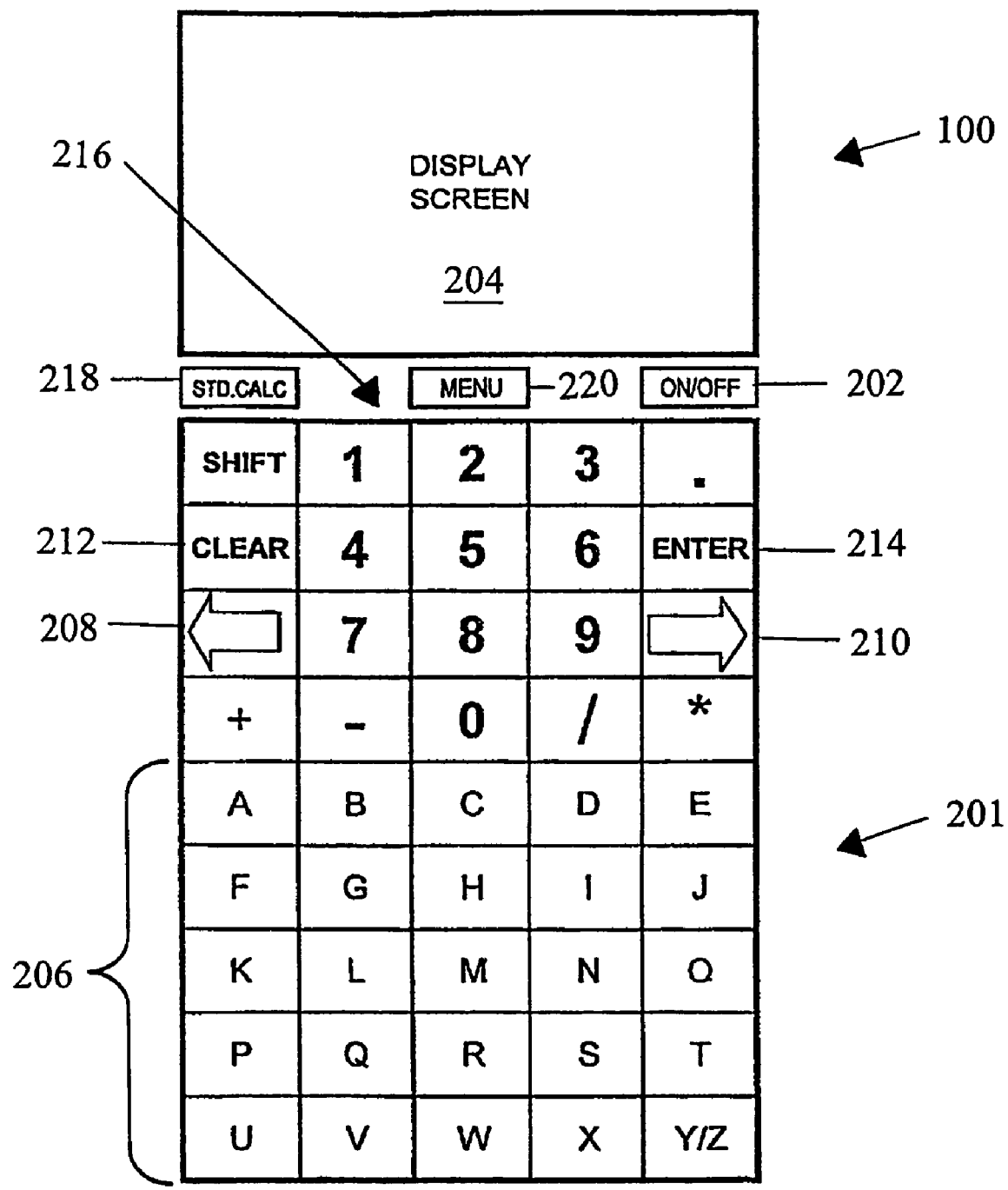
FIG. 4 illustrates a top view of a sample keyboard and display screen associated with the handheld medication dosage calculator of the present invention.

The first step in the process <12> is to activate or turn-on the handheld medication dosage calculator that is generally indicated by numeral 100 in FIG. 4. The on/off pushbutton 202, as shown in FIG. 4, performs this function. This reveals a display screen 204, which displays the graphical user input and output medication screen that is generally indicated by numeral 101 in FIG. 2. A graphical user interface provides an intuitive input for the information that greatly reduces the need for the user to rely on his or her memory in performing the sequence of keypad operations on the handheld medication dosage calculator.

The display screen 204 is preferably a liquid crystal display; however, any electronic display can be employed for the purposes of this patent application such as a cathode ray tube (CRT), an electroluminiscent display or a plasma display.

Figure 2:
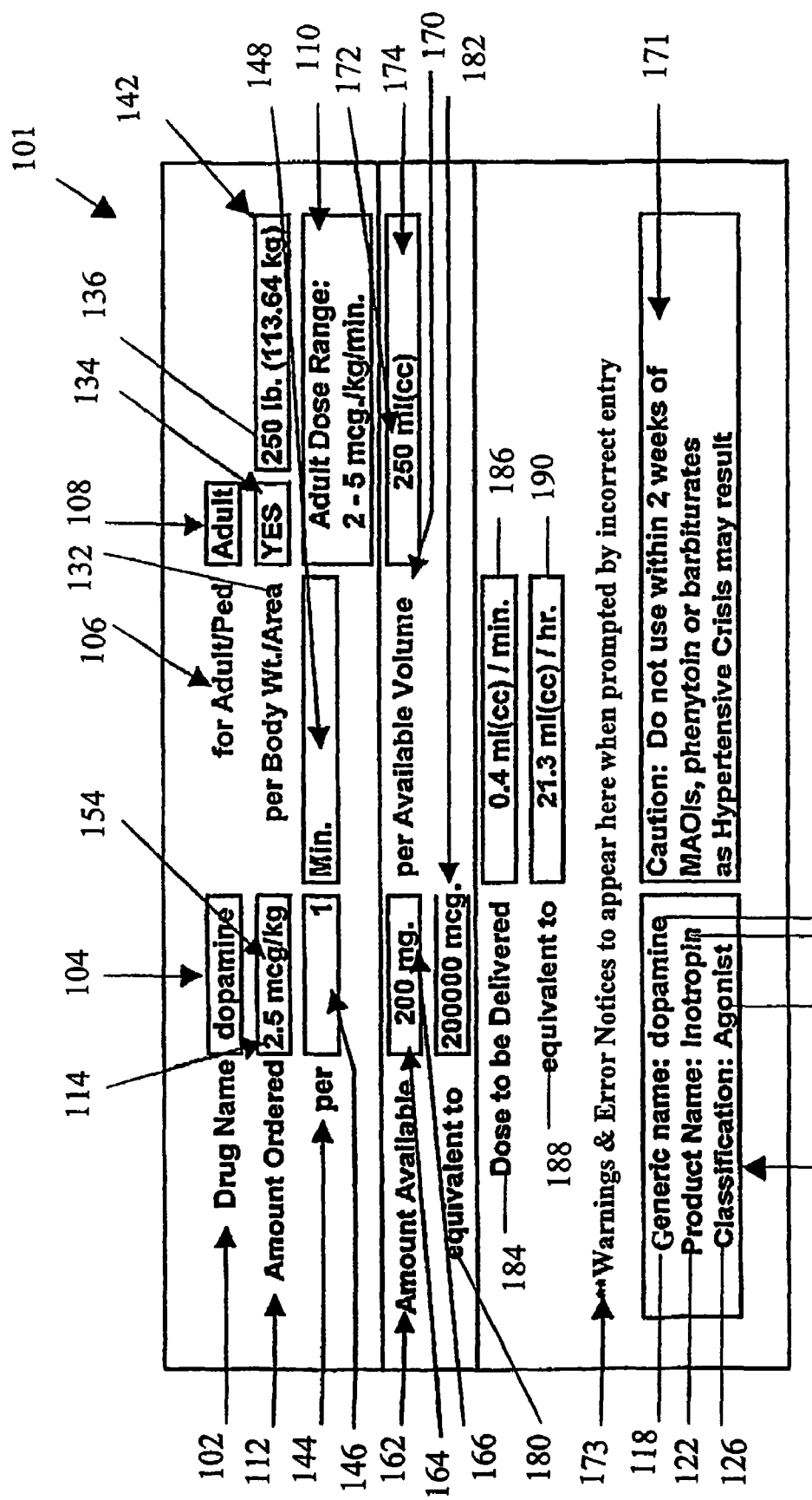
FIG. 2 illustrates an exemplary graphical input and output screen display of a handheld medication dosage calculator associated with the present invention.

As shown in FIG. 2, there is an output for the name of the desired drug, e.g., "drug name" label 102, that is adjacent to a drop-down entry input for the desired drug name 104 that is preferably highlighted and includes a flashing cursor. Pressing one of the alphabetic keys 206 on the handheld medication dosage calculator 100, as shown on FIG. 4, will initiate the drop-down entry input for the desired drug name 104 to reveal a selection of available drugs, as indicated by a drop-down selection 150 in FIG. 3.

The second step in the process <14>, as shown in FIG. 1A, is to determine if the desired drug is available. This involves scrolling among the drop-down selection 150, shown in FIG. 3, by utilizing either the left scroll arrow key 208 or the right scroll arrow key 210 on the handheld medication dosage calculator 100, as shown in FIG. 4.

If the desired drug is not available, the "clear entry" key 212 can be pushed, as shown in FIG. 4 and the second step in the process <14> can be repeated so that the user can again search for a desired drug. This "clear entry" procedure is indicated by the third step in the process <16>, as shown in FIG. 1A, which loops back to the second step in the process for inputting a desired drug <14>. If the desired drug is not in the system, then a blank can be inputted into the system through the enter key 214, as shown on FIG. 4, as indicated by the fourth step in the process <21>, as shown in FIG. 1A, which bypasses the next process step <17> and proceeds to process step <18>, as shown on FIG. 1A. In this specific instance, the tenth process step <26> of providing warnings if the drug dosage exceeds a recommend range is also bypassed (not shown).

Figure 3:
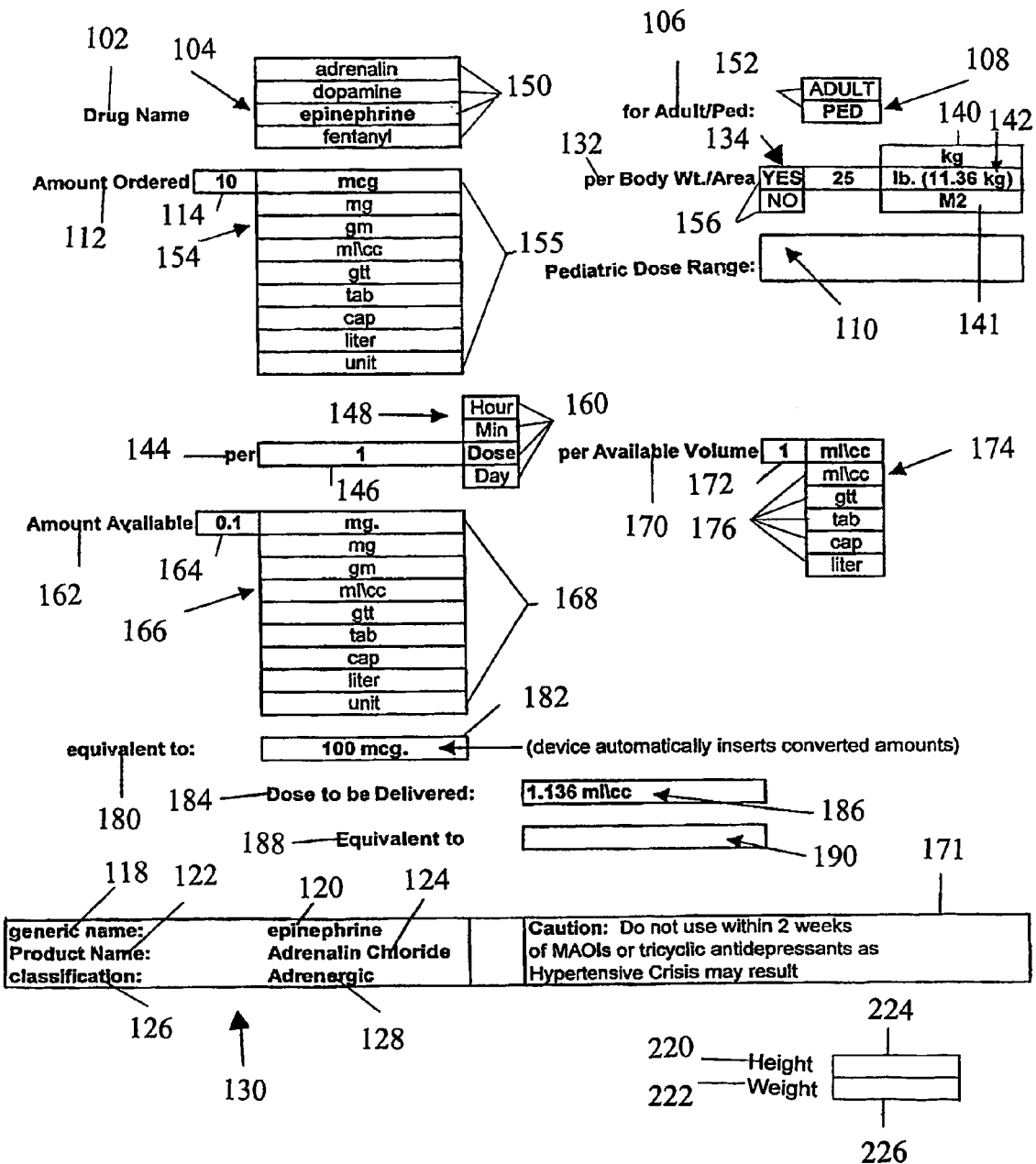
FIG. 3 illustrates exemplary drop-down screen displays connected with the exemplary screen display shown in FIG. 2 associated with the handheld medication dosage calculator of the present invention.
Figure 5:
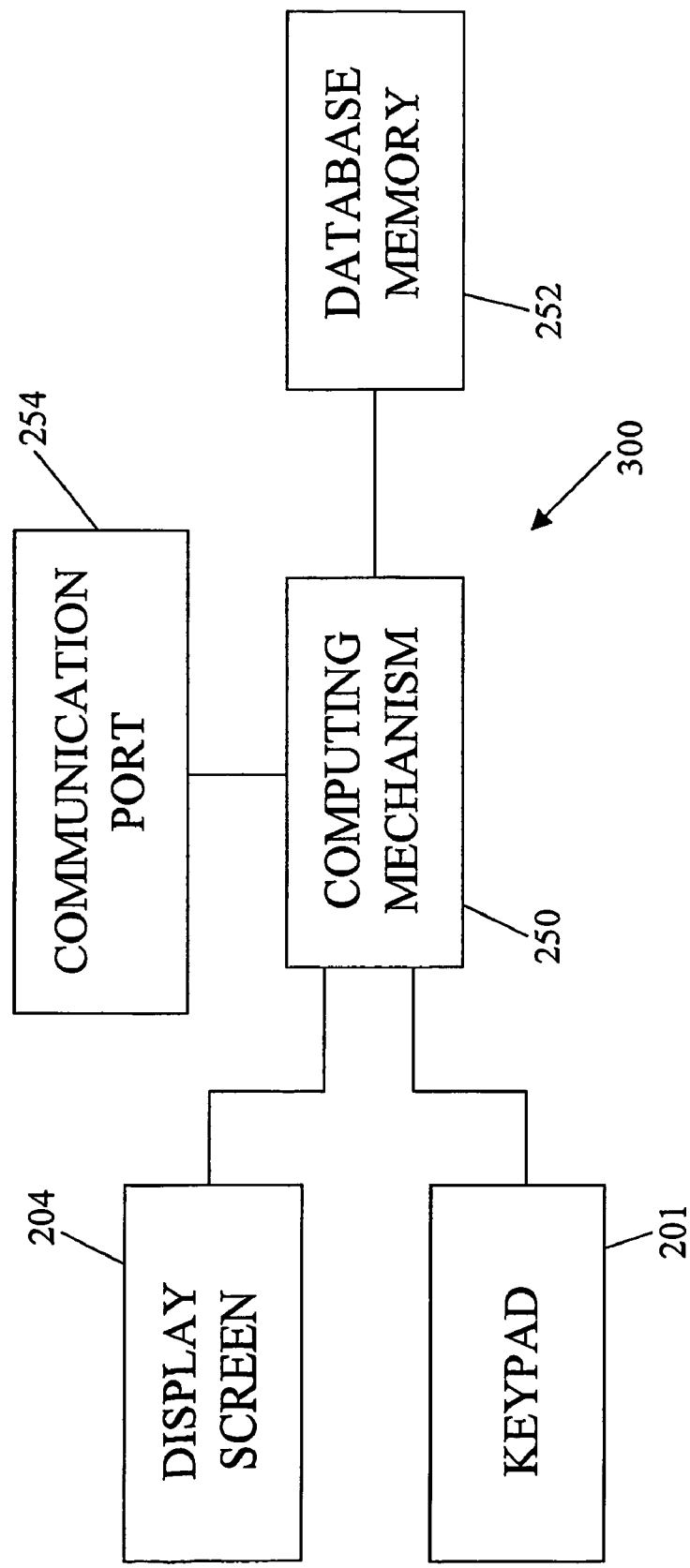
FIG. 5 illustrates a block diagram of a basic functional schematic for the electronic components associated with the handheld medication dosage calculator of the present invention.

The fifth step in the process <17>, as shown in FIG. 1A, is to select the desired drug and view associated output information. If the desired drug is located on the drop-down selection 150, as shown in FIG. 3, which is then preferably highlighted, the user can then press the "enter" key 214 for the handheld medication dosage calculator 100 shown in FIG. 4. There is an output for the generic name of the desired drug, e.g., "generic name" label 118, that is adjacent to an output for the generic name of the drug 120. There is also an output for the trademarked product name of the desired drug, e.g., "product name" label 122, that is adjacent to an output for the trademarked product name for the drug 124. Moreover, there is an output for the appropriate classification associated with the desired drug, e.g., "drug classification" label 126, that is adjacent to an output for the classification associated with the desired drug 128. These three labels 118, 122 and 126 and associated outputs 120, 124 and 128 appear in an output screen that is generally indicated by numeral 130 in FIGS. 2 and 3. There is also cautionary material associated with the selected drug that is displayed in output screen 171. This information is provided by the database memory 252 and provided to the computing mechanism 250 for display on the display screen 204, as shown in FIG. 5, which is a block diagram schematic that indicates the general electronic components and associated relationship for the handheld medication dosage calculator 100 that is generally indicated by numeral 300.

The sixth step in the process <18>, as shown in FIG. 1A, is to determine if the selected drug will be administered to a child or an adult. There is a output regarding whether the drug is to be administered to a child or an adult, e.g., adult/pediatric label 106, that is adjacent to an adult/pediatric drop-down entry input 108 regarding selection of whether it is a child or an adult, which is preferably highlighted and includes a flashing cursor, as shown in FIG. 2, where a drop-down adult/pediatric selection 152 appears as shown in FIG. 3. The user can scroll between the two possible selections in the adult/pediatric drop-down selection 152, shown in FIG. 3, by utilizing either the left scroll arrow key 208 or the right scroll arrow key 210 on the handheld medication dosage calculator 100, as shown in FIG. 4. When the desired patient type, i.e., pediatric or adult, is located on the adult/pediatric drop-down selection 152, as shown in FIG. 3, the user can then press the "enter" key 214 on the handheld medication dosage calculator 100 shown on FIG. 4.

When this selection is made, the program will either go to either the seventh process step <20>if the patient is an adult or to the eighth process step <22>if the patient is a child, as shown in FIG. 1A.

The proper range for either adult or pediatric dosages will appear as output 110, as shown in FIGS. 2 and 3.; Preferably, when the patient type is a child, i.e., pediatric, the calculations will appear three places past the decimal point, which can be utilized in dosage calculations.

The ninth step in the process <24>, as shown in FIG. 1A, is to input the desired dosage for the selected drug. As shown in FIG. 2, there is an output for the amount of drug ordered, e.g., "amount ordered" label 112, that is adjacent to a drug amount ordered input 114 that preferably is highlighted and includes a flashing cursor, as shown in FIG. 2. By pressing the numeric keys on the handheld medication dosage calculator 100, which keys are generally indicated at 216 on FIG. 4, the user can input the desired amount of drugs to be dispensed. Adjacent to the drug amount ordered input 114 is a unit expression factor drop-down entry input 154 that is preferably highlighted and includes a flashing cursor, as shown in FIG. 2, where a drop-down unit expression factor selection 155 appears as shown in FIG. 3. The user can scroll between the possible units of measurement in the unit expression factor selection 155, shown in FIG. 3, by utilizing either the left scroll arrow key 208 or the right scroll arrow key 210 on the handheld medication dosage calculator 100, as shown in FIG. 4. When the desired unit of measurement is located on the drop-down unit expression factor selection 155, as shown in FIG. 3, the user can then press the "enter" key 214 on the handheld medication dosage calculator, as shown on FIG. 4.

The tenth step in the process <26>, as shown in FIG. 1B, is to determine if the drug dosage exceeds the recommend range. If the quantity inputted though the drug amount ordered input 114 exceeds that for the selected patient type, i.e. adult or child, then a warning is issued as the eleventh process step <28>. This is done by comparing the inputted quantity data from the keypad 201 with range information from the database memory 252 in the computing mechanism 250 for the handheld medication dosage calculator 100, as shown in FIG. 5. This step could occur later in the process if the warning is dependent on patient weight and/or frequency of drug administration.

This issued warning appears on an output screen 173, as shown in FIG. 2. If a warning is issued, then the twelfth process step <30>allows the user to clear the drug amount entry and returns the user to the ninth process step <24>, which allows the user to re-enter the desired drug dosage. However, you may perform the calculation without inputting a desired drug and still calculate a drug dosage and bypass the system of warnings and outputted information that is available with a selected drug.

The thirteenth step in the process <32>, as shown in FIG. 1B, is to determine if the drug dosage should be analyzed based on either the body weight of the patient or the body surface area of the patient. There is, an output for either the body weight of the patient or the body surface area of the patient, e.g., per body wt./area label 132, that is adjacent to an body wt./area drop-down elective input 134 that is preferably highlighted and includes a flashing cursor, as shown in FIG. 2, where a drop-down body wt./area selection 156 appears as shown in FIG. 3. The user can scroll between the two possible selections, i.e., yes or no, in the body wt./area drop-down selection 156, shown in FIG. 3, by utilizing either the left scroll arrow key 208 or the right scroll arrow key 210 for the handheld medication dosage calculator 100, as shown in FIG. 4.

The fourteenth step in the process <33>, as shown in FIG. 1B, is to determine if the drug dosage will be based on the patient's weight or the body surface area of the patient. There is a body weight/area data entry input 136, which is adjacent to the body wt./area drop-down selection input 134. By pressing the numeric keys 216 on the handheld medication dosage calculator 100, which are generally indicated on FIG. 4, the user can input the weight of the patient or the body surface area of the patient. Adjacent to the body weight/area data entry input 136 is a weight/body area drop-down selector 142 that allows the user to input the weight of the patient in kilograms 140 or the body surface area of the patient in square meters 141. The user can scroll between the two possible selections, i.e., the weight of the patient in kilograms 140 or the body surface area of the patient in square meters 141 shown in FIG. 3, by utilizing either the left scroll arrow key 208 or the right scroll arrow key 210 on the handheld medication dosage calculator 100, as shown in FIG. 4.

If the dosage of the drug is based on body weight, then the numerical input in the body weight/area data entry input 136 is entered when the user presses the "enter" key 214 after previously selecting "yes" from the drop-down body wt./area selection 156 on the handheld medication dosage calculator 100 as shown on FIGS. 3 and 4, which is the fifteenth step in the process <34>, as shown in FIG. 1B.

The weight of the patient can be either in pounds (lbs.) or kilograms (kgs.), and appears in output 142 with converted amounts appearing adjacent to the selected weight expression unit. This process involving conversion is the sixteenth step in the process <36>, as shown in FIG. 1B.

If the body surface area of the patient in square meters 141 is selected, an output for the height of the patient, e.g., height of patient label 220, along with an input for the height of the patient, e.g., patient height input 224, appears as well as an output for the weight of the patient, e.g., patient weight label 222, along with a patient weight input 226, as shown in FIG. 3, through data input provided by the numeric keys 216 on the handheld medication dosage calculator 100, which are generally indicated in FIG. 4, which is the seventeenth process step <38>shown in FIG. 1B. This data is utilized by the computing mechanism 250 with information from the database memory 252 to arrive at the body area in square meters ($m^2$) that is displayed in output 142.

The eighteenth step in the process <39>, as shown in FIG. 1C, is to enter the frequency for applying the drug dosage. There is an output for the frequency of providing the drug to the patient, e.g., "per" frequency label 144, that is adjacent to a frequency data input 146 that is preferably highlighted and includes a flashing cursor, as shown in FIGS. 2 and 3. This frequency is inputted through a data input provided by the numeric keys 216, which are generally indicated in FIG. 4. Adjacent to the frequency data input 146 is the frequency expression factor drop-down elective input 148. The user can scroll among a number of possible frequency selections 160 including hour, minute, day and so forth, shown in FIG. 3, by utilizing either the left scroll arrow key 208 or the right scroll arrow key 210 on the handheld medication dosage calculator 100, as shown in FIG. 4. The computing mechanism 250 converts the data from the keypad 201 if inputted in either days or minutes into an hourly rate, as shown in FIG. 5.

When the desired unit of frequency interval is selected through inputting the frequency data input 146 and the unit-expression factor selection 154, as shown in FIG.3, the user can then press the "enter" key 214 as shown on FIG. 4.

The nineteenth step in the process <40>, as shown in FIG. 1C, is for the user to enter the amount of the selected drug that is available in standard packaging for the patient. There is an output to indicate the amount of the drug that is available in standard packaging, e.g., "amount available" label 162, that is adjacent to a drug amount available input 164 that is preferably highlighted and includes a flashing cursor, as shown in FIG. 2. By pressing the numeric keys 216 on the handheld medication dosage calculator 100, which are generally indicated on FIG. 4, the user can input the desired amount of drugs that are available. Adjacent to the drug amount available input 164 is a unit expression factor drop-down entry input 166 that is preferably highlighted and includes a flashing cursor, as shown in FIG. 2 where a drop-down unit expression factor selection 168 appears as shown in FIG. 3. The user can scroll between the possible units of measurement in the unit expression factor selection 168, shown in FIG. 3, by utilizing either the left scroll arrow key 208 or the right scroll arrow key 210 on the handheld medication dosage calculator 100, as shown in FIG. 4. When the desired unit of measurement is located on the drop-down unit expression factor selection 168, as shown in FIG. 3, the user can then press the "enter" key 214 as shown on FIG. 4. Conversions to the appropriate unit of measurement will be automatically performed by the computing mechanism 250, as shown in FIG. 5.

In addition, the twentieth step in the process <41>, as shown in FIG. 1C, is to covert the amount available from the drug amount available input 164 into an equivalent number that is in a desired unit of measurement. There is an output for an equivalent amount of the drug in a preferred unit of measurement, e.g., "equivalent to" label 180, that is adjacent to a converted drug amount output 182. Conversions to the desired unit of measurement will be automatically performed by the computing mechanism 250 and displayed on the display screen 204 for the handheld medication dosage calculator 100, as shown in FIG. 5. If incompatible unit expression factors are entered, the handheld medication dosage calculator 100 will not perform the calculation until the error is fixed.

The twenty-first step in the process <42>, as shown in FIG. 1C, is to enter the volume of the selected drug that is available for the patient for the amount of drug that is available. There is an output for indicating the volume associated with the amount of available drug in standard packaging, e.g., "per available volume" label 170 that is adjacent to a volume of the available drug input 172 that is preferably highlighted and includes a flashing cursor, as shown in FIG. 2. By pressing the numeric keys 216 on the handheld medication dosage calculator 100, which are generally indicated on FIG. 4, the user can input the available volume for the amount of the selected drug that is available. Adjacent to the volume of the available drug input 172 is a unit expression factor drop-down entry input 174 that is preferably highlighted and includes a flashing cursor, as shown in FIG. 2 where a drop-down unit expression factor selection 176 appears as shown in FIG. 3. The user can scroll between the possible units of measurement in the unit expression factor selection 176, shown in FIG. 3, by utilizing either the left scroll arrow key 208 or the right scroll arrow key 210 on the handheld medication dosage calculator 100, as shown in FIG. 4. When the desired unit of measurement is located on the drop-down unit expression factor selection 176, as shown in FIG. 3, the user can then press the "enter" key 214 on the handheld medication dosage calculator 100 as shown on FIG. 4. Conversions to the appropriate unit of measurement will be automatically performed by the computing mechanism 250, as shown in FIG. 5.

The twenty-second step in the process <44>, as shown in FIG. 1C, is to compute the dosage of the drug to be administered. This includes multiplying the amount of the drugs that are ordered from the drug amount ordered input 114 times the body weight or the body surface area from the body weight/area data entry input 136. This product is then divided by the amount of drugs that are available from the drug amount available input 164. This result is then multiplied by the volume of the drug from the amount available that can be administered to the patient from the volume of the available drug input 172. This result is the dosage of the drug to be delivered to the patient. Preferably, this output should be calculated in less than two seconds.

The twenty-third step in the process <46>, as shown in FIG. 1C, is to output the dosage of the drug to be administered computed in the previous process step <44>. There is an output to indicate the drug dose to be delivered to the patient, e.g., "dose to be delivered" label 184 that is adjacent to a delivered drug dosage output 186.

In addition, the twenty-fourth step in the process <47>, as shown in FIG. 1C, is to convert the drug dosage from the drug amount available input 164 into an equivalent number in a desired unit of measurement for drug administration frequency. This is only triggered when the frequency selection 160 of the drug dosage is determined on a "per minute", a "per hour" or a "per day" basis and not when the "per dose" input is selected. As shown in FIGS. 2 and 3, there is an output for this for the drug dosage in the preferred unit of measurement, e.g., "equivalent to" label 188 that is adjacent to a converted drug dosage to be delivered in a preferred measurement unit 190. Conversions to the desired unit of measurement for the handheld medication dosage calculator 100 will be automatically performed by the computing mechanism 250 and displayed on the display screen 204, as shown in FIG. 5.

The user then administers the appropriate amount of drugs to the patient and the software program is then completed <48>as the twenty-fifth process step.

Referring now to FIG. 4, there is a calculator pushbutton key 218, which allows the handheld medication dosage calculator 200 to function as a standard calculator as well as a menu pushbutton key 220 that allows the user to access other functions of the handheld medication dosage calculator 200.

Preferably, there is some type of device to update the database memory 252 as shown in FIG. 5. For example, a communication port 254 could be connected to the computing mechanism 250 for updating the database memory 252. An example of how this can be accomplished is described in U.S. Pat. No. 6,266,539, which issued to Pardo on Jul. 24, 2001, which is incorporated herein by reference. This is a docking arrangement that connects the computing mechanism 250 to the Internet via a telephone communication line.

Another mechanism can include a PCMCIA card for receiving a chip card such as that disclosed in U.S. Pat. No. 6,069,795, which issued to Klatt et al. on May 30, 2000, which is incorporated herein by reference. The chip card could have a static read only memory (ROM) that includes the database memory 252.

Infrared sensors can also be utilized to update the database memory 252. An example of this type of technology can be found in U.S. Pat. No. 6,025,942, which issued to Scifres on Feb. 15, 2000, which is incorporated herein by reference.

These are just some of the illustrative, but nonlimiting, examples of the many types of technology that can achieve this function of updating the database memory 252.

Figure 6:
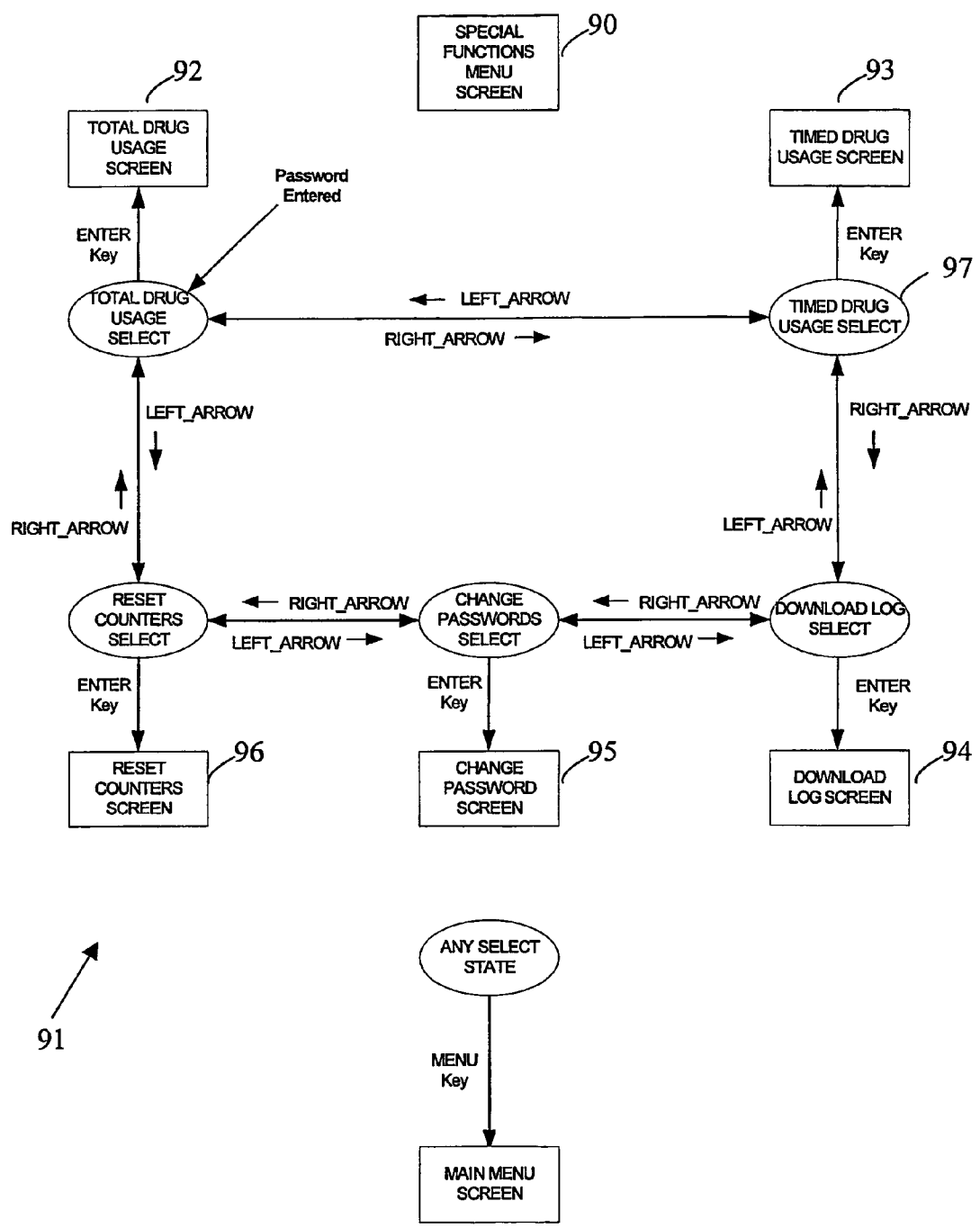
FIG. 6 illustrates a schematic process diagram of the special functions menu screen of the handheld medication dosage calculator.

Referring now to FIG. 6, a hidden special functions password entry screen 90 is displayed in the display screen 204. The special functions screen 90 provides the user with a single box to enter a password. The password may be between one and ten characters in length. The characters being entered by the user is not displayed, rather a '#' symbol is displayed instead for each character entered. When the password is entered and the ENTER key is pressed, the password is compared to the special functions password and the special function master password. If either matches, the password screen is closed and the special functions screen 90 menu is displayed. If there is no match, a message indicating password incorrect is displayed and the password entry box is cleared so that the user can try again. Initially, there is no limit to the number of failed attempts, but this feature is easily added by one skilled in the art. A single CLEAR key press clears all characters currently entered in the password entry box. Selection of the MENU key at any point shall close the password screen and return to the Menu Options screen.

A special functions menu options screen 91 has five options for selection as follows: a total drug usage option 92; a timed drug usage option 93; a download warning log option 94; a change passwords option 95; and a reset usage counters option 96. The left and right arrows keys enable the user to scroll up and down the options list, and the current cursor position shall be highlighted with a dark background and white text. Pressing the ENTER key will select the currently highlighted option and display the appropriate screen. Selection of the MENU key at any point will close the special functions Menu Options screen 91 and return the user to the main menu options screen.

The total drug usage option 92 screen displays the current values for the following counters: 1) total usage; 2) total number of decimal entries in the digital display screen 204; 3) individual drug usage; 4) total number of outside of range warning occurrences; 5) total number of outside of range warning occurrences that were overridden by the user; 6) total number of outside of range warning occurrences that were corrected by the user; 7) total number of no range check warning occurrences; 8) total number of no range check warning occurrences that were overridden by the user; 9) total number of no range check warning occurrences that were corrected by the user; 10) total number of conversion error occurrences; and 11) total number of conversion error occurrences that were corrected by the user.

Individual drug usage totals are selectable by selecting the drug from a list of available drugs. To select a drug, the user starts typing in the drug name in the drug selection 70 box. Upon entry of the first letter of the drug, the display screen 204 displays a list of all available drugs and will automatically jump to and highlight the first drug listed which starts with the letter entered. As the user enters more letters, the display screen 204 will automatically highlight the closest match. When the user presses the ENTER key, the currently highlighted drug in the list will be selected, and the drug list will close. However, after the entry of one or more letters into the drug selection 70 box but before the ENTER key is pressed, the user is able to move into the drug list by pressing the left or right arrow keys. When this occurs, the left and right arrow keys shall then move the cursor highlight up and down through the drug list respectively. At any point, pressing the ENTER key shall select the currently highlighted drug as the active drug, and close the drug list. The available drug list is displayed in alphabetical order.

When a drug has been selected, its total usage value is read from the drug database file and displayed adjacent to the selected drug name. Selection of the MENU key at any point will close the total drug usage screen 92 and return the user to the special functions menu screen 90.

The timed drug usage screen 93 will display the current values for the following shift counters: 1) number of outside of range warning occurrences in the shift period; 2) number of outside of range warning occurrences that were overridden by the user in the shift period; 3) number of outside of range warning occurrences that were corrected by the user in the shift period; 4) number of no range check warning occurrences in the shift period; 5) number of no range check warning occurrences that were overridden by the user in the shift period; 6) number of no range check warning occurrences that were corrected by the user in the shift period; 7) number of conversion error occurrences in the shift period; and 8) number of conversion error occurrences that were corrected by the user in the shift period.

A timed drug usage screen 97 displays the Shift Time Period, and the date/time that the current shift is due to end, and a option to view the counts for the current shift or each of the previous 3 shifts. The user is able to set the Shift Time Period to between one and twenty-four hours in one hour increments by typing in the value required and then pressing the ENTER key to set this value entered. When the Shift Time Period is changed, a confirmation required message will be displayed informing the user that changing the Shift Time Period will cause all previous shift data to be lost. The message shall provide the user with a yes/no option to continue and change the time period or to cancel the operation. If yes is selected (confirm change to time period), all shift counters shall be reset and the new current shift shall commence from the current time. If no is selected, the message shall be closed and the user returned to the timed drug usage screen 97 with no action taken. From the Shift Time Period entry box, the left or right arrow key when pressed will activate a selection list to display shift period counters. When the list is active, the left and right arrow keys shall then move the cursor up/down the list items. Pressing the ENTER key selects the shift period counters to display. At any point, if the '+' key is pressed a sub-screen shall be displayed listing the last four entries in the warning/event log. When the warning/event log display sub-screen is active, the user is able to close it and return to the timed drug usage screen 93 by pressing the ENTER or CLEAR key.

Selection of the MENU key at any point will close the timed drug usage screen 97 and return the user to the special functions menu screen 90.

The selection of the download warning/event log option will cause the handheld calculator 100 to copy the warning/event log to a text file on a PCMCIA card. When the file copy has finished, a download complete message is displayed informing the user. If the handheld calculator 100 is unable to copy the log to a PCMCIA (i.e. no card inserted), a message is displayed informing the user. Once again, the updating of the database can be updated by other means as explained above. When the user acknowledges whichever message is displayed, the message is closed and the user returned to the special functions menu screen 90.

The change passwords screen 95 provides the user with the options of changing the special function menu 90 entry password and the reset counters confirmation password. The left and right arrow keys will toggle between the two new password entry boxes. The ENTER key shall indicate the completion of the entry of a new password if the password entry box contains one to ten characters. When a valid new password has been entered, the user is prompted with a sub-screen to enter the current password as confirmation that they wish to change to the new password. When a confirmation password has been entered (followed by ENTER), the handheld calculator 100 checks the confirmation password against the stored current password and if they match replaces the stored password when the new password entered. If the confirmation password does not match the stored current password, the display screen 204 will display an incorrect password message and clear the entry box ready for the user to try again. Initially, there is no limit to the number of failed attempts the user is allowed to make. At any point, selection of the MENU key cancels the action and return the user to the special functions menu 10 screen 90.

Upon selection of the reset counters option 96, the handheld calculator 100 prompts the user to enter a reset counters confirmation password. When a confirmation password has been entered (following by ENTER key), the handheld calculator 100 checks the confirmation password entered against the stored current password and if they match all total and timed counters are set to zero. Once this is complete, a message is displayed indicating that all counters have been successfully reset. When the user acknowledges this message (ENTER key), the message is closed, and the user returned to the special functions menu screen 90. If the confirmation password does not match the current stored reset counters password, the display screen 204 displays an incorrect password message and clears the entry box ready for the user to try again. Initially, there is no limit to the number of failed attempts the user is allowed to make. At any point, selection of the MENU key cancels the action and returns the user to the special functions menu screen 90.

Figure 7:
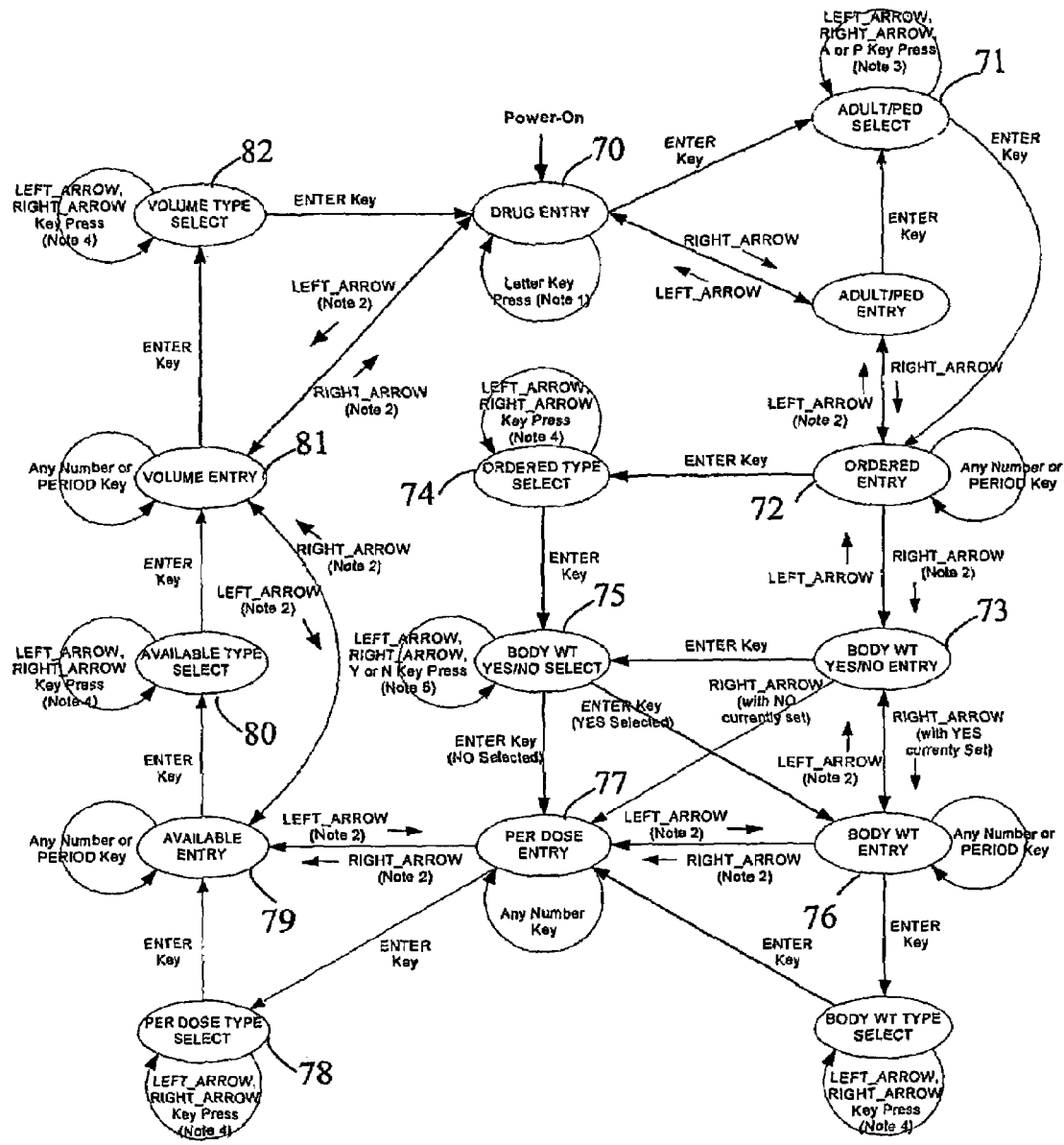
FIG. 7 illustrates an alternative schematic process diagram of the handheld medication dosage calculator.

Referring now to FIG. 7, the display screen 204 of the handheld calculator 100 displays various functions. The display screen 204 has a default screen on start-up. The display screen 204 has the following functional options: drug selection 70;

adult or pediatric selection 71; ordered type entry 72; overall ordered type selection 74 of either mcg, mg, gm, units or mEq, with mg as default; body weight/area—yes or no selection 73; body weight/area value entry 75 (but only when yes selected for 73); body weight/area type selection 76 of either lb, kg, gm or $m^2$, with lb as default (but only when yes selected 73); dose/time quantity 77 with default value of 1; dose/time type selection 78 of either per dose, min, hour or day, with dose as default; amount available quantity 79; amount available type selection 80 of either mcg, mg, gm, units or mEq, with mg as default; available volume quantity 81; and available volume type selection 82 of either liter, cc, tab or gtt, with cc as default. When all of the required parameters have been entered by the user, the application will perform a dose calculation. The required parameters are ordered type entry 72, overall ordered type selection 74 of either mcg, mg, gm, units or mEq, with mg as default, body weight/area value entry 75 (but only when yes selected for 73); body weight/area type selection 76 of either lb, kg, gm or $m^2$, with lb as default (but only when yes selected 73); dose/time quantity 77 with default value of 1; amount available quantity 79; amount available type selection 80 of either mcg, mg, gm, units or mEq, with mg as default; available volume quantity 81; and available volume type selection 82 of either liter, cc, tab or gtt, with cc as default. The data parameters can be entered in any order. For the dose calculation, the handheld calculator 100 uses the following pharmaceutical formula for calculating the dose to deliver based on the data parameters entered by the user:

$$\text{Dose} = (\text{Total Amount Ordered}/\text{Amount Available}) * \text{Volume}$$

where the Total Amount Ordered can be equal to either:
a) Amount Ordered
b) Amount Ordered*Body Weight (in kg)
c) Amount Ordered*(Body Weight (in kg)/Time)

The dose calculation is to be 'circular,' meaning that once all required parameters have been entered, the changing of any one parameter will cause a re-calculation of the dose to deliver and the displaying of any new warning message if appropriate. A drug does not have to be selected in order to perform a dose calculation. During dose calculation, if the overall ordered type selected 74 does not match the amount available type selected 80, the handheld calculator 100 displays a conversion error message and the ordered type entry 72 box becomes the active control. (Note: any combination of mcg, mg and gm is considered a match). The drug database file contains up to three dose ranges for each drug, each range with a different ordered type (e.g. 1–4 mg/dose, 20–50 mcg/kg/dose and 5–7 mcg/kg/min). During dose calculation, the overall ordered type 74 is first matched against the database range types. If no match of the overall ordered type 74 against the database range type can be found, the handheld calculator 100 displays a range check warning message indicating the problem. The message also provides the user with a yes/no option of continuing with no range checking or changing the ordered type 74.

If yes is selected (to continue with no range checking), the calculated dose is displayed and the warning LED's set to a flashing mode to indicate that the ordered amount has not been checked against the recommended ranges. If no is selected, the calculated dose is discarded and the ordered type entry 72 box becomes the active control.

When the ordered type 72 matches one of the database range types, the total ordered amount is checked against the range values. If the total ordered amount is either higher or lower than the range values, the display screen 204 displays a dosage warning message. The message provides the user with a yes/no option of continuing with the current total amount ordered or changing the amount ordered. If yes is selected (to continue with current amount ordered), the calculated dose is displayed and the warning LED's set to a flashing mode to indicate the total amount ordered is outside the recommended drug range. If no is selected, the calculated dose shall be discarded and the ordered entry 72 box becomes the active control. There are two exceptions to this when performing the ordered type/database range type matching. The first exception occurs if the user has entered a body weight/area value 75, but the database range type does not have /kg but otherwise they match (e.g. ordered mg/kg/dose but database has mg/dose). In this case, a flag is set and if no match is then subsequently found the handheld calculator 100 calculates the total amount ordered (by multiplying the amount ordered by the body weight in kg) and then performs a range check as though the ordered type was in mg/dose. The second exception occurs if the ordered type does not have a body weight/area value 75 but the database range type does but otherwise they match (e.g. ordered mg/dose but database has mg/kg/dose). In this case, another flag is set and if no match is subsequently found, a warning message is displayed informing the user that no range checking could be performed but could be if the user entered the patients estimated body weight. The message also provides the user with a yes/no option of continuing without range checking or to enter the patients estimated body weight. If yes is selected (to continue without range checking), the calculated dose is displayed and the warning LED's set to flashing to indicate that the ordered amount has not been check against recommended ranges. If no is selected, the calculated dose is discarded and the body weight/area yes/no option 73 is automatically set to yes and the body weight/area value entry 75 box then becomes the active control.

The total amount ordered (Amount Ordered*Body Weight in kg) is displayed when the user has selected a body weight/area value in the calculation. If the ordered quantity is over a time period (i.e. min, hour or day), then when the dose is successfully calculated the handheld calculator 100 is also calculated expanded rates to include: i/cc/min; ii/cc/hour; iii/dose/min; iv/dose/hour; v/dose/kg/min; and vi/dose/kg/min. If the-user has entered no body weight, the last two rates shall show 'NA'.

The expanded rates are displayed on a separate sub-screen, which appear when the user presses the '*' key. Once the sub-screen is active, the 'ENTER' key clears it. When expanded rates are available and there is room on the display screen 204, a message is displayed indicating that to view the expanded rates the user must press the '*' key. Only the ENTER key submits a new parameter for validation. If the value entered is valid, the handheld calculator 100 either calculates the dose to deliver (only if all other required parameters have been entered) or moves to the next parameter entry/type selection. Dose calculations only occur after a new quantity value and its associated type have been entered. The left and right arrow keys are used to scroll quickly around the display screen 204 without causing any data entry or dose re-calculations to occur. The current cursor position (active control) is indicated by a dark background with white text. When scrolling with the left and right arrow keys, the adult/pediatric and yes/no lists are not displayed. Type selection lists are displayed when their associated entry box is scrolled upon but the lists themselves are not part of the scroll order. Using the drug selection 70; adult or pediatric selection 71; ordered type entry 72; ordered type selection 74 of either mcg, mg, gm, units or mEq, with mg as default; body weight/area—yes or no selection 73; body weight/area value entry 75 (but only when yes selected for 73); body weight/area type selection 76 of either lb, kg, gm or m$^2$, with lb as default (but only when yes selected 73); dose/time quantity 77 with default value of 1; dose/time type selection 78 of either per dose, min, hour or day, with dose as default; amount available quantity 79; amount available type selection 80 of either mcg, mg, gm, units or mEq, with mg as default; available volume quantity 81; and available volume type selection 82 of either liter, cc, tab or gtt, with cc as default items, the left and right arrow scroll order is the drug selection 70; adult or pediatric selection 71; ordered type entry 72, body weight/area—yes or no selection 73, body weight/area value entry 75 (but only if option body weight/area—yes or no selection 73 is set to yes), dose/time quantity 77, amount available quantity 79 and available volume quantity 81. While scrolling adult/pediatric and yes/no, a selection is achieved by scrolling onto the current value and pressing the ENTER key. The list will then appear with the non-active value selected as default.

When a list selection is the active control, the left and right arrow keys move the selection cursor up and down the list, respectively. The list will only be exited when the ENTER key is pressed, upon which the highlighted list item is selected and becomes the active value. All list selection controls wrap-around from top to bottom and bottom to top. When a drug is selected, the data for that drug is read from the drug database file and populates the drug information sub-screen which may be displayed at any time in the display screen 204 by the user pressing the '+' key. When a drug is selected, the first dose range for this drug from the database is displayed at the top of the display screen 204. If no dose range exists for the selected drug, a message indicates that no dose range is available for this drug. The drug information sub-screen when active is only cleared by the pressing of the ENTER or CLEAR key once. Upon returning to the display screen 204, the control that was active prior to the '+' key being pressed regains active control. The application stores the last used amount available and available volume values within the record for the currently selected drug in the drug database file. If no drug is selected, these value will not be stored. When the user re-selects a drug that has saved amount available and available volume values, the application displays a message informing the user of the stored value and offering the yes/no option of using these values or entering new values. If yes is selected (use stored values), the amount available quantity 79 entry box and available volume quantity 81 entry box is automatically populated with the stored value. However, this message will only appear when the user has just finished selection of a dose/time type selection 78. When the user enters a body weight in lb or grams, the application converts the entered value into kg and displays this value adjacent to the entered value.

Once a dose has been calculated and a warning message issued, the same warning message will only be displayed again if the amount ordered value is changed or the dose calculated is different then previous. Upon re-entry to the display screen 204 (after the user has been in the Calculator or Menu screens), the active control is the same control that was active immediately prior to the display screen 204 being exited. To select a drug the user starts typing in the drug name in the drug selection 70 box. Upon entry of the first letter of the drug, the handheld calculator 100 displays a list of all available drugs and automatically jumps to and highlights the first drug listed which starts with the letter entered. As the user enters more letters, the handheld calculator 100 will automatically highlight the closest match. When the user presses the ENTER key, the currently highlighted drug in the list is selected and becomes the active drug, the drug list closes and the adult/pediatric list becomes the next active control. At this point, the information for this drug reads from the database file and formatted ready for display and the '*' key option becomes active. After the entry of one or more letters into the drug selection 70 box but before the ENTER key is pressed, the user is able to move into the drug list by pressing the left or right arrow keys. When this occurs, the left and right arrow keys then move the cursor highlight up and down through the drug list, respectively. At any point, pressing the ENTER key selects the currently highlighted drug as the active drug, closes the drug list and the adult/pediatric list becomes the next active control. At this point, the information for this drug reads from the database file and formatted ready for display and the '*' key option becomes active. The available drug list is displayed in alphabetical order. Decimal values are valid for all quantity parameters except the dose/time parameter, which are an integer value. All dose calculations with the pediatric selection are displayed-to three decimal places. All dose calculations with the adult selection are displayed to two decimal places. A single CLEAR key press clears any value entered in the currently active control if the control is one of the entry boxes. If the CLEAR key is pressed twice with the second key press within approximately one second of the first key press, all entered values are cleared and the screen reverts to its default state. Selection of the MENU key at any point displays the Menu Options screen. Selection of the MATH CALC key at any point displays the basic calculator screen.

The following is a summary of the main functions to be performed by the handheld calculator 100. The handheld calculator 100's display screen 204 allows the user to select a drug and enter various data parameters. Once all required data has been entered, it performs the necessary calculations to generate a dose to deliver value. While calculating the dose, the quantity of the selected drug ordered is checked against the recommended range limits for the particular drug selected from the drug database file. Appropriate warning messages are displayed depending on the result of the calculation and range checking. Information on the drug selected can also be viewed. The Conversions Screen allows the users to perform some basic conversions for mcg to/from mg, lb to/from kg and ml to/from liters. A surface area (m²) formula is also provided. The Drip Rate Calculator allows the user to perform Drip Rate and Infusion Rate calculations. The Database Update allows the user to update the drug database file on the unit via the unit's PCMCIA slot. It is important to note that that Database Update can be accomplished by other means (e.g., Internet, Infrared, etc.) as explained above. The Basic Calculator provides a basic math calculator so the user can perform basic multiplication, division, addition and subtraction functions. The Warning/Event Log logs all warning events and other system events. The Usage & Warning Counters allow the user to view a total count of all warning messages issued and whether the warning was corrected or overridden. It also provides the user with the counts for the same warnings but over a set period of time (shift). The current shift and the three previous shifts can be viewed.

INDUSTRIAL APPLICABILITY

The present invention is advantageously applicable in providing a handheld medication dosage calculator 100, which significantly improves the safety and efficacy of dispensing medicine by reducing the user's reliance on memory. Moreover, this handheld medication dosage calculator 100 simplifies the user algorithm and provides constraints and forcing functions that significantly reduce the reliance on vigilance and multiple data entry. This is also a more intuitive approach to calculating drug dosages by providing a user algorithm that is located on the display screen 204. Furthermore, the drug information data stored in the database memory 252 is linked to the input data to elicit predetermined warnings and cautions when the input deviates from known dosage range information. This is in addition to providing an output for the recommend dosage of drugs.

This results in a device that significantly reduces the chance of medication error as well as reduces the amount of time needed to dispense drugs to patients by a medical professional.

The invention in its broader aspects is not limited to the specific steps or apparatus shown and described, but departures may be made therefrom without deviating from the principles of the invention and without sacrificing its chief advantages. Other aspects, objects and advantages of the present invention can be obtained from a study of the drawings and the disclosure.

What is claimed is:

1. A portable medical calculator for automatically calculating a medication dose and comparing an inputted, ordered medication dosage with a known medication dosage range in a database, comprising:
   a display screen for prompting and receiving certain inputs, receiving entered data, receiving answers to medical questions, displaying various selections for selection, displaying various units of measure, displaying calculations and displaying warning messages;
   memory operatively connected to the display screen for receiving and comparing the inputted, ordered medication dosage with the known medication dosage range;
   a computing mechanism operatively connected to the memory and the display screen, the computing mechanism;
   responsive to the inputs, data, answers, selections and unit of measures at the display screen to cause the memory to provide the medication dose;
   responsive to the inputted, ordered medication dosage to cause the memory to compare the inputted, ordered medication dosage with the known medication dosage range;
   responsive to the comparison to cause the memory to provide the warning messages to the display screen when the inputted, ordered medication dosage is outside the known medication dosage range; and
   responsive to the warning messages to cause the memory to request additional data via the display screen to correct the inputted, ordered medication dosage or continue without correction of the inputted, ordered medication dosage when the warning messages are activated.

2. The portable medical calculator for automatically calculating a medication dose and comparing an inputted, ordered medication dosage with a known medication dosage range in a database according to claim 1, wherein the display screen displays a number of times the inputted, ordered medication dosage is outside the known medication dosage range for a certain predetermined period of time.

3. The portable medical calculator for automatically calculating a medication dose and comparing an inputted, ordered medication dosage with a known medication dosage range in a database according to claim 2, wherein the display screen displays a number of times the inputted, ordered medication dosage is corrected when the warning messages are activated to within the known medication dosage range for the predetermined period of time.

4. The portable medical calculator for automatically calculating a medication dose and comparing an inputted, ordered medication dosage with a known medication dosage range in a database according to claim 2, wherein the display screen displays a number of times the inputted, ordered medication dosage is used when the warning messages are activated without correction of the inputted, ordered medication dosage to within the known medication dosage range for the predetermined period of time.

5. A portable medication dose calculator for comparing an inputted, ordered medication dosage with a known medication dosage range in a database, comprising:

an input device for inputting a desired medication name, inputting an indication as to whether the medication is for a child or an adult, inputting an amount of the medication that is ordered, inputting the body weight or body surface area of the patient;

inputting an amount of medication that is available, and inputting the available volume associated with the amount of the available medication;

a computing mechanism for automatically determining the appropriate dose of the medication that is to be administered to the patient and converting the determined dose that is to be administered to the patient and available dosage into desired units of measure; and a display for displaying the appropriate dose of the medication, displaying cautionary warnings if the selected medication amount exceeds a recommended range of the medication provided in the medication database, displaying product names and classifications for each selected medication, and displaying cautionary product information associated with each selected medication.

6. The portable medication dose calculator for comparing an inputted, ordered medication dosage with a known medication dosage range in a database according to claim 5, wherein the computing mechanism converts the final medication dose into a preferred unit of measure.

7. The portable medication dose calculator for comparing an inputted, ordered medication dosage with a known medication dosage range in a database according to claim 5, further including means for updating the database.

8. The portable medication dose calculator for comparing an inputted, ordered medication dosage with a known medication dosage range in a database according to claim 5, further including a communications system for updating the database from an Internet via a telephone communication line.

9. The portable medication dose calculator for comparing an inputted, ordered medication dosage with a known medication dosage range in a database according to claim 5, further including a PCMCIA card and a chip card having a static read only memory (ROM) for updating the database, wherein the PCMCIA card receives the chip card with an updated database.

10. The portable medication dose calculator for comparing an inputted, ordered medication dosage with a known medication dosage range in a database according to claim 5, further including infrared sensors for updating the database.

11. A medication dose calculator or computer for comparing an inputted, ordered medication dosage with a known medication dosage range in a database, comprising:

a display screen for displaying a plurality of drop down screens, data input fields, output display fields, warning display fields and caution display fields;

memory operatively connected to the display screen, the memory containing the database having the known medication dosage range, the drop down screens, the data input fields, the output fields, the warning display fields and the caution display fields;

means for viewing and navigating through a plurality of medications listed by name from a medication name drop down menu on the display screen;

means for selecting a specific medication by name from the drop down menu on the display;

a computing mechanism operatively connected to the memory and the means for selecting the specific medication responsive to the selection of the specific medication;

means for displaying a name of the specific medication from the memory on the display screen;

means for displaying a classification of the specific medication from the memory on the display screen;

means for displaying cautionary information associated with the specific medication from the memory on the display screen;

an adult/pediatric drop down menu on the display screen for selecting an adult or pediatric patient status;

the computing mechanism operatively connected to the memory and the adult/pediatric drop down menu and responsive to the adult or pediatric patient status selection for displaying the medication dose at a medication dose output field on the display screen;

means for inputting a ordered medication dosage for the selected medication in a ordered medication dosage field on the display screen;

a unit of measure drop down menu on the display screen adjacent the ordered medication dosage field for selecting a ordered unit of measure of the ordered medication dosage;

the processor for comparing the inputted, ordered medication dosage with a recommended range of medication dosages for the selected medication and patient status, the processor sending a warning to the display screen if the inputted, ordered medication dosage is outside the recommended range;

a body weight/body surface area drop down menu for designating if a body weight or body surface calculation is applicable to the selected medication and activating a body weight/body surface input display field;

means for inputting a body weight or body surface area value if the body weight/body surface input display field is activated;

body weight/body surface area unit of measure drop down menu on the display screen adjacent the body weight/body surface area input display field for selecting a desired weight unit of measure;

means for inputting a patient's body weight and height in a body weight input field and a body height input field, respectively;

the computing mechanism operatively connected to the memory and the body weight/body surface area input display field and the body weight/body surface unit of measure drop down menu and responsive to the inputted and selected data on the display screen for calculating the patient's body surface area;

a medication dosage frequency drop down menu for selecting a frequency period for administering the selected medication;

means for inputting a number in a medication dosage frequency input field, the number indicative of the frequency the selected medication will be administered during the frequency period;

means for inputting an amount of the medication available in a medication availability input field on the display screen;

a medication availability unit of measure drop down menu on the display screen adjacent the medication availability input field for selecting an availability unit of measure of the selected medication;

the computing mechanism operatively connected to the memory, the medication availability input field and the medication availability unit of measure drop down menu for converting the unit of measure of the medication amount available to the unit of measure used for the ordered medication dosage and displaying the medication availability number in converted unit of measure in an equivalent output field on the display screen;

means for inputting a volume of the selected medication available for the amount of the medication that is available in a volume availability input field;

a volume unit of measure drop down menu on the display screen adjacent the volume availability input field for selecting a volume unit of measure; and the computing mechanism operatively connected to the memory, the display screen, the medication dosage range output field, the body weight input field or body surface area input field, the equivalent output field and the volume availability input field for automatically calculating and displaying on the display screen the final medication dose to be administered to the patient.

12. The medication dose calculator for comparing an inputted, ordered medication dosage with a known medication dosage range in a database according to claim 11, wherein the computing mechanism converts the final medication dose into a preferred unit of measure.

13. The medication dose calculator for comparing an inputted, ordered medication dosage with a known medication dosage range in a database according to claim 11, further including means for updating the database.

14. The medication dose calculator for comparing an inputted, ordered medication dosage with a known medication dosage range in a database according to claim 11, further including a communications system for updating the database from an Internet via a telephone communication line.

15. The medication dose calculator for comparing an inputted, ordered medication dosage with a known medication dosage range in a database according to claim 11, further including a PCMCIA card and a chip card having a static read only memory (ROM) for updating the database, wherein the PCMCIA card receives the chip card with an updated database.

16. The medication dose calculator for comparing an inputted, ordered medication dosage with a known medication dosage range in a database according to claim 11, further including infrared sensors for updating the database.

17. A method for comparing an inputted, ordered medication dosage with a known medication dosage range in a database, comprising the steps of:

displaying a plurality of drop down screens, data input fields, output display fields, warning display fields and caution display fields on a display screen;

operatively connecting memory to the display screen, the memory containing the database having the known medication dosage range, the drop down screens, the data input fields, the output fields, the warning display fields and the caution display fields;

viewing and navigating through a plurality of medications listed by name from a medication name drop down menu on the display screen;

selecting a specific medication by name from the drop down menu on the display;

displaying a trademark name of the specific medication from the memory on the display screen;

displaying a generic name of the specific medication from the memory on the display screen;

displaying a classification of the specific medication from the memory on the display screen;

displaying cautionary information associated with the specific medication from the memory on the display screen;

selecting an adult or pediatric patient status on an adult/pediatric drop down menu;

automatically computing and displaying the medication dose at a medication dose output field on the display screen;

inputting an ordered medication dosage for the selected medication in an ordered medication dosage field on the display screen;

selecting an ordered unit of measure of the ordered medication dosage on a unit of measure drop down menu on the display screen adjacent the ordered medication dosage field;

comparing the inputted ordered medication dosage with a recommended range of medication dosages for the selected medication and patient status;

sending a warning to the display screen if the inputted ordered medication dosage is outside the recommended range;

designating if a body weight or body surface area calculation is applicable to the selected medication via a body weight/body surface area drop down menu and activating a body weight/body surface input display field;

inputting a body weight or body surface area value if the body weight/body surface input display field is activated;

selecting an ordered weight unit of measure via a body weight/body surface area unit of measure drop down menu on the display screen adjacent the body weight/body surface area input display field;

inputting a patient's body weight and height in a body weight input field and a body height input field, respectively;

computing and calculating the patient's body surface area;

selecting a frequency period for administering the selected medication;

inputting a number in a medication dosage frequency input field, the number indicative of the frequency the selected medication will be administered during the frequency period;

inputting an amount of the medication available in an availability medication input field on the display screen;

selecting an availability unit of measure of the selected medication via a medication availability unit of measure drop down menu on the display screen adjacent the medication availability input field;

computing and converting the unit of measure of the medication amount available to the unit of measure used for the ordered medication dosage and displaying the medication availability number in a converted unit of measure in an equivalent output field on the display screen;

inputting a volume of the selected medication available for the patient for the amount of the medication that is available in a volume availability input field; selecting a volume unit of measure; and automatically computing, calculating and displaying on the display screen a final medication dose to be administered to the patient.

18. The method for comparing an inputted, ordered medication dosage with a known medication dosage range in a database according to claim 17, further comprising the steps of computing and converting the final medication dose into a preferred unit of measure.

19. The method for comparing an inputted, ordered medication dosage with a known medication dosage range in a database according to claim 17, further comprising the step of updating the database.

20. A portable device for automatically calculating a medication dose and comparing an inputted, ordered medication dosage with a known medication dosage range, comprising:

a display screen for displaying a plurality of preconfigured prompts and medical information;

an input mechanism operatively associated with said display screen, and for selecting choices among the preconfigured prompts, and inputting medical data;

a memory operatively connected to the input mechanism and display screen, the memory containing said plurality of preconfigured prompts and storing the known medication dosage range; and a processor connected to the display screen, the memory, and the input mechanism, for comparing the inputted, ordered medication dosage with the known medication dosage range; for sending a warning message to the display screen when the inputted, ordered medication dosage is outside the known medication dosage range; and for permitting continuation with or without correction of the inputted, ordered medication dosage when the warning message is activated.

21. A portable device as set forth in claim 20, wherein the warning message is displayed without disabling the display screen.

22. A portable device for automatically calculating a drug dose in a clinical setting, the drug dose being defined as a calculated volume required to deliver an ordered dosage from a larger volume available in specified concentration and the dosage being definded as an amount of medicine by a) quantity of measure, b) quantity of measure per weight, c) quantity of measure per time or d) quantity of measure per weight and time, including:

a computer having a memory;

means for entering data into the computer upon which the drug dose is calculated;

the computer having means for automatically calculating the calculated volume required to deliver an ordered dosage from a larger volume available in specified concentration in response to the entered data;

a display screen for displaying the calculated dose volume; and the device being capable of calculating doses from all four types of said quantities of measure a) through d).

23. The portable device for automatically calculating a drug dose in a clinical setting, as set forth in claim 22, wherein the display screen for displaying the calculated volume does not display the mathematical formula therefor.

24. The portable device for automatically calculating a drug dose in a clinical setting, as set forth in claim 23, wherein the computer checks the dosage ordered against a dosage database.

* * * * *